US00PP13483P2

(12) United States Plant Patent
Vandenberg

(10) Patent No.: US PP13,483 P2
(45) Date of Patent: Jan. 14, 2003

(54) CHRYSANTHEMUM PLANT NAMED 'LIGHT MOOD'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 22 days.

(21) Appl. No.: 09/899,970

(22) Filed: Jul. 9, 2001

(51) Int. Cl.[7] ..... A01H 5/00

(52) U.S. Cl. ..... Plt./289

(58) Field of Search ..... Plt./289, 287

*Primary Examiner*—Howard J. Locker
(74) *Attorney, Agent, or Firm*—C. A. Whealy

(57) ABSTRACT

A distinct cultivar of Chrysanthemum plant named 'Light Mood', characterized by its large quilled decorative-type inflorescences that are about 13.75 cm in diameter; attractive golden yellow-colored inflorescences; response time about 61 days; dark green foliage; strong and thick stems; and excellent postproduction longevity with inflorescences maintaining good substance and color for about three to four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Light Mood'.

The new Chrysanthemum is a product of a mutation induction breeding program conducted by the Inventor in Alva, Fla. The objective of the program is to create new Chrysanthemum cultivars having inflorescences with desirable colors and good form and substance.

The new Chrysanthemum is a naturally-occurring whole plant mutation of a proprietary induced mutation that originated by exposing unrooted cuttings of the Chrysanthemum cultivar Mood, disclosed in U.S. Plant Pat. No. 12,935, to X-ray radiation at a dose of 2,000 rads. The new Chrysanthemum was discovered and selected by the Inventor as a single flowering plant within a population of plants of the irradiated selection in November, 1998 in Alva, Fla. The selection of this plant was based on its desirable inflorescence color and good form and substance.

Asexual reproduction of the new Chrysanthemum by terminal cuttings taken in a controlled environment in Alva, Fla. since February, 1999, has shown that the unique features of this new Chrysanthemum are stable and reproduced true to type in successive generations.

SUMMARY OF THE INVENTION

Plants of the cultivar Light Mood have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Light Mood'. These characteristics in combination distinguish 'Light Mood' as a new and distinct cultivar:

1. Upright cut Chrysanthemum that is typically grown as a disbud.

2. Large quilled decorative-type inflorescences that are about 13.75 cm in diameter.

3. Attractive golden yellow-colored inflorescences.

4. Response time about 61 days.

5. Dark green foliage.

6. Strong and thick stems.

7. Excellent postproduction longevity with inflorescences maintaining good substance and color for about three to four weeks in an interior environment.

Plants of the new Chrysanthemum are most similar to plants of the cultivar Mood. However, plants of the new Chrysanthemum differ primarily from plants of the cultivar Mood in ray floret color as ray florets of the cultivar Mood are golden bronze in color.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Light Mood' grown as a disbud.

The photograph on the second sheet comprises a close-up view of a typical flowering stem of 'Light Mood' grown as a disbud.

DETAILED BOTANICAL DESCRIPTION

In the following description, color references are made to The Royal Horticultural Society Colour Chart except where general terms of ordinary dictionary significance are used. The aforementioned photographs and following observations and measurements describe plants grown in La Ceja, Antioquia, Colombia, South America, under conditions which approximate commercial practice in a single-layer polyethylene-covered greenhouse. Two-week old rooted cuttings were planted on Dec. 26, 2000 and received 14 long day/short nights followed by short day/long nights until flowering. Plants were grown as single-stem disbud cut Chrysanthemums. During the production time, the following environmental conditions were measured: day temperatures, 20 to 27° C.; night temperatures, 8 to 13° C.; and light levels, 4,000 to 6,000 foot-candles. Measurements and numerical values represent averages for six to ten typical flowering stems and were taken about 9 to 10 weeks after the start of short days.

Botanical classification: *Chrysanthemum×morifolium* cultivar Light Mood.

Commercial classification: Quilled decorative-type cut Chrysanthemum.

Parentage: Naturally-occurring whole plant mutation of a proprietary *Chrysanthemum×morifolium* induced mutation, not patented.

Propagation:

*Type*.—Terminal tip cuttings.

*Time to rooting*.—About 10 to 14 days with soil temperatures of 18 to 21° C.

*Root description*.—Fine, fibrous and well-branched.

Plant description:

*Appearance*.—Herbaceous quilled decorative-type cut flower that is typically grown as a disbud.

*Flowering stem description*.—Aspect: Erect. Length: About 90 cm. Diameter (base of stem): About 6.5 mm. Internode length: About 4.5 cm. Texture: Densely pubescent; longitudinally ridged. Color: Close to 146A.

*Foliage description*.—Arrangement: Alternate. Length: About 11.2 cm. Width: About7.5 cm. Apex: Cuspidate. Base: Attenuate. Margin: Palmately lobed; sinuses parallel to convergent. Texture: Upper and lower surfaces pubescent; smooth and leathery; veins prominent on lower surface. Color: Young foliage upper surface: Darker than 147A. Young foliage lower surface: Darker than 147B. Mature foliage upper surface: Darker than 147A. Mature foliage lower surface: Close to 147B. Venation, upper surface: 147A to 147B. Venation, lower surface: 147B. Petiole: Length: About 2 cm. Diameter: About 4 mm. Color: Upper surface: 147A to 147B. Lower surface: 146B.

Flowering description:

*Appearance*.—Decorative-type inflorescence form with elongated quilled-shaped ray florets. Inflorescences borne on terminals, arising from leaf axils. Disc and ray florets arranged acropetally on a capitulum.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 61 days later when grown as a disbud.

*Postproduction longevity*.—In an interior environment, flowering stems will maintain good color and substance for about three to four weeks in an interior environment after one week of cool storage.

*Quantity of inflorescences*.—When grown as a disbud, one per flowering stem, as the terminal inflorescence bud is the only one that is not removed.

*Inflorescence size*.—Diameter: About 13.75 cm. Depth (height): About 3.8 cm. Diameter of disc: About 3 mm, inconspicuous. Diameter of receptacle: About 1.4 cm.

*Ray florets*.—Shape: Elongated, quilled. Length: About 7.1 cm. Width: About 5 mm. Corolla tube length: About 5.9 cm. Apex: Emarginate. Base: Fused. Texture: Satiny, smooth, glabrous; slightly longitudinally ridged. Aspect: Initially incurved; when mature, perpendicular to peduncle; mostly straight, curved upward at apex. Number of ray florets per inflorescence: About 335 arranged in numerous rows. Color: When opening: Initially green, 144B to 144C, then 13A to 12A with faint 163A overtones. Mature, throat: 12A to 15A. Mature tube: 13A to 12A with faint 163A overtones.

*Disc florets*.—Shape: Tubular, elongated. Length: About 6 mm. Width: Apex: About 1.5 mm. Base: About 1 mm. Number of disc florets per inflorescence: Few, massed at center of receptacle, usually fewer than 10. Color: Immature: 144A to 144B. Mature: Apex and mid-section: 9A. Base: 155D.

*Reproductive organs*.—Androecium: Present on disc florets only. Anther color: Close to 12A. Amount of pollen: None observed. Gynoecium: Present on both ray and disc florets.

*Seed*.—Seed production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. Plants of the new Chrysanthemum do not tolerate high temperatures greater than 40° C.

It is claimed:

1. A new and distinct cultivar of Chrysanthemum plant named 'Light Mood', as illustrated and described.

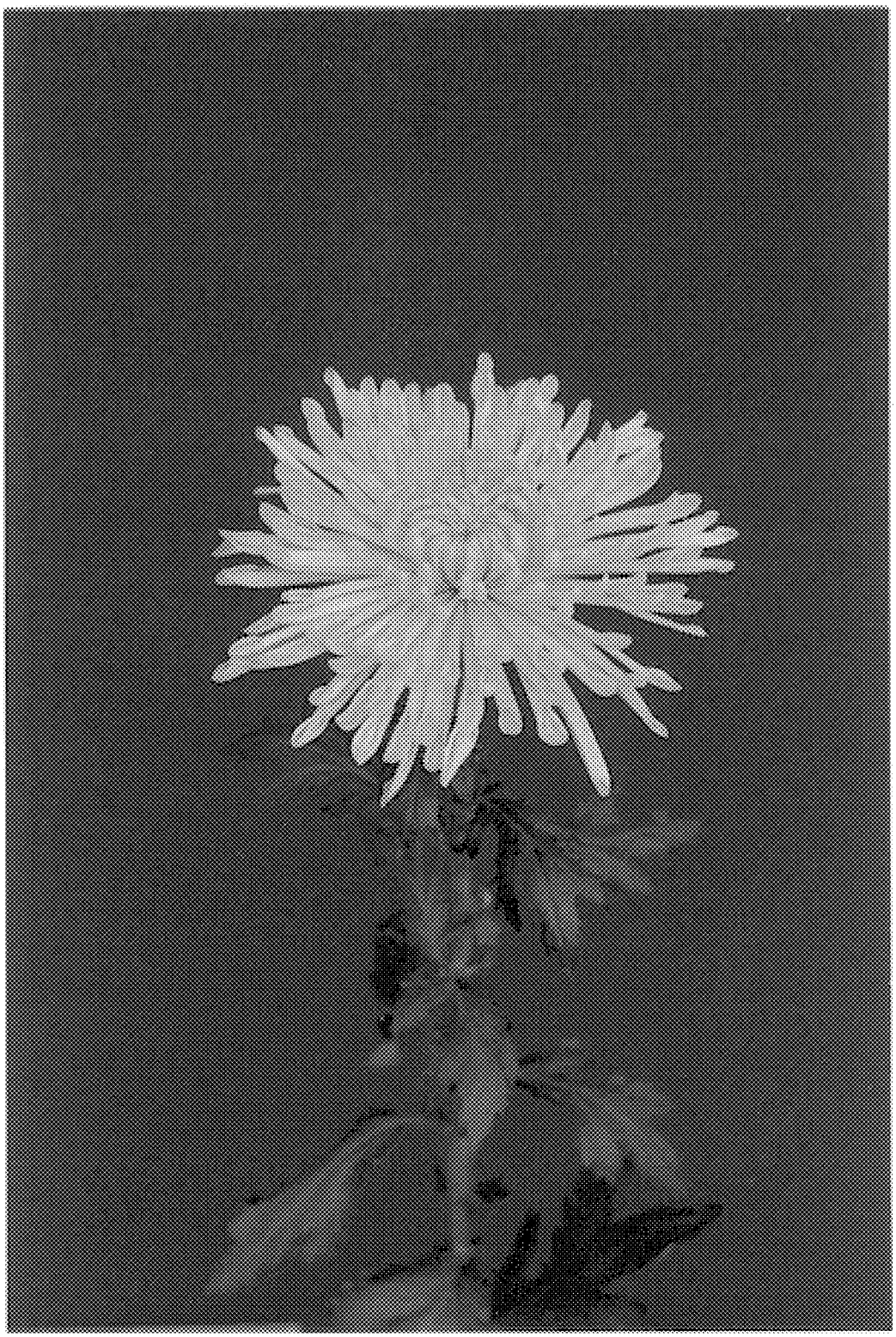

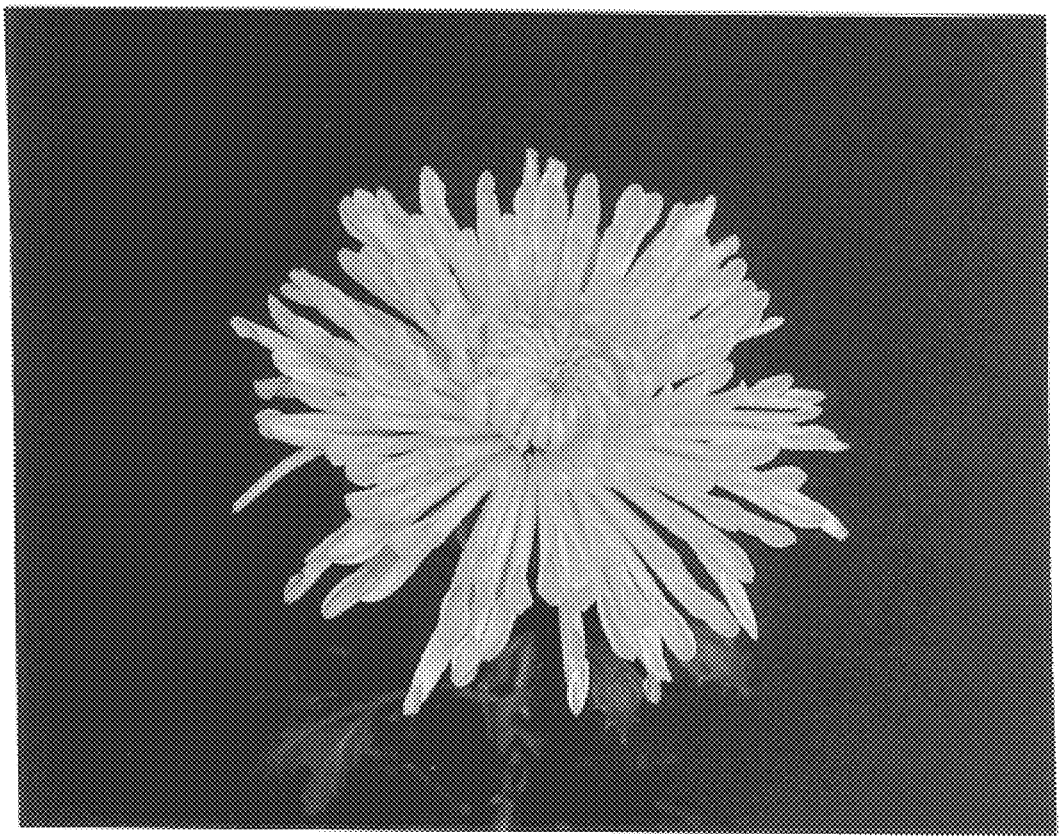

* * * * *